United States Patent [19]

Tomalia et al.

[11] Patent Number: 4,600,535
[45] Date of Patent: Jul. 15, 1986

[54] CYCLIC PEPTIDES

[75] Inventors: Donald A. Tomalia; Larry R. Wilson, both of Midland, Mich.

[73] Assignee: The Dow Chemical Company, Midland, Mich.

[21] Appl. No.: 659,201

[22] Filed: Oct. 9, 1984

Related U.S. Application Data

[62] Division of Ser. No. 348,528, Feb. 12, 1982.

[51] Int. Cl.[4] .......................... C07D 257/02
[52] U.S. Cl. ............................. 260/239.3 R
[58] Field of Search ............... 260/112.5 S, 112.5 R, 260/239.3 R

[56] References Cited

PUBLICATIONS

Rich et al., *J.A.C.S.*, 100, 2212-2218 (1978).
Christensen et al, *Science* 174, No. 4008, 459-467 (1971).
Tsuboyama et al., *Tet. Lett.*, 16, 1367-1370 (1970).
Hey et al., *Inorganic Chimica Acta*, 59, 147-153 (1982).
Hansen et al., *J. Hetrocyclic Chem.*, 5, 305 (1968).
Chemical Abstracts 68, (1968), Abst. No. 45774a.

*Primary Examiner*—Delbert R. Phillips
*Assistant Examiner*—F. T. Moezie

[57] ABSTRACT

Cyclic peptides, such as 1,4,8,11-tetraazacyclotetradecane-5,12-dione, that are useful chelation agents for metals are prepared by contacting an acrylic acid ester and a 1,2-alkylenediamine.

5 Claims, No Drawings

CYCLIC PEPTIDES

CROSS-REFERENCE TO RELATED APPLICATION

This is a divisional, of application Ser. No. 348,528, filed Feb. 12, 1982.

BACKGROUND OF THE INVENTION

The present invention relates to cyclic peptide compounds also referred to as macrocyclic polypeptides. In particular, the present invention relates to cyclic peptides containing alanine moieties. The invention further relates to a process for making the novel cyclic peptides of the invention.

Numerous cyclic peptide compounds are known or have been described in the art. Previously however, the synthetic methods employed have been tedious and complicated requiring the use of expensive reactants and suffering from low yields of the desired cyclic peptide product.

Examples of known cyclic peptides include L-Pro[1]-tentoxin disclosed by D. Rich et al., *J.A.C.S.*, 100, 2212 (1978). The compound was prepared by standard blocking and deblocking techniques followed by intramolecular cyclization in pyridine solvent.

It is also known to cyclo oligomerize N-alkyl aziridines with various cationic initiators such as $BF_3$ or paratoluene sulfonic acid to give tetraazacyclodecanes; see, e.g., S. Tsuboyama et al., *Tet. Lett.*, 16, 1367–1370 (1970); G. R. Hansen et al., *J. Heterocyclic Chem.*, 5, 305 (1968).

In U.S. Pat. No. 3,305,493, linear polymers of an acrylic acid ester and a polyalkylenepolyamine are disclosed. The linear polymers were formed by heating a Michael addition product of the acrylic acid ester and the polyalkylenepolyamine to a temperature of from about 90° C. to about 130° C. A similar process is disclosed by U.S. Pat. No. 3,445,441.

SUMMARY OF THE INVENTION

According to the present invention are provided novel cyclic peptide compositions corresponding to the formula

  (I)

wherein R and R' indepenently each occurrence are hydrogen or $C_{1-4}$ alkyl.

Further included in the invention is a novel process for preparing the invented cyclic peptide compositions comprising contacting an ester of acrylic acid or an ester of a substituted acrylic acid with a 1,2-alkylenediamine under conditions conductive to the formation of a Michael addition product and subsequently subjecting the Michael addition product to conditions conductive to the intermolecular and intramolecular amidation thereby forming the linear dimeric reaction product and cyclic peptide respectively.

The invented compounds are useful in forming chelates with metal ions such as copper, iron or zinc ions thereby aiding in solubilizing such metals in various systems. The compounds furthermore have been found to possess useful insecticidal properties.

DETAILED DESCRIPTION OF THE INVENTION

The invented cyclic peptides of previously described formula (I) are easily prepared by reaction of an acrylic ester and a 1,2-alkylenediamine. Suitable acrylic esters are those of the formula $CH_2=CR'CO_2R''$ wherein R'' is a $C_{1-8}$ normal alkyl radical, and R' is as previously defined. Examples include methyl acrylate, ethyl acrylate, n-butyl arcylate, methyl methacrylate, ethyl methacrylate, n-octyl ethyl acrylate, etc. Preferred esters are methyl acrylate, ethyl acrylate, methyl methacrylate and ethyl methacrylate. A most preferred reactant is methyl acrylate.

The 1,2-alkylenediamines are those of the formula $NH_2CRHCRHNH_2$ wherein R is a previously defined. Examples include ethylenediamine, 1,2-propylenediamine, 2,3-butylenediamine, etc. A preferred reactant is ethylenediamine.

The Michael addition reaction is easily effected by merely contacting the two reactants, preferably without a solvent, at a temperature from about −10° C. to about 80° C. Temperatures in excess of 80° C. tend to lead to production of longer chain linear oligomers instead of the desired cyclic compounds. Preferred reaction temperatures are from about 20° C. to about 60° C.

The ratio of ester to diamine reactants is from about 1:1 to about 1:7. Generally, excess diamine is removed by vacuum distillation following complete addition of ester reactant to prevent formation of additional amine adducts. A solvent is not normally required but may be employed if desired.

The Michael addition product,

readily undergoes subsequent intermolecular and intramolecular amidation reactions to form first the linear dimeric reaction product,

and then the cyclic polypeptide product,

It is only required that the Michael addition product be retained at a temperature of from about 10° C. to about 60° C. for a time sufficient to allow the elimination of two equivalents of the hydroxyl compound to occur. Reaction times of up to several weeks may be required for the cyclization process to occur. Removal of the hydroxyl by-product, as by vacuum distillation, and purification of the product, as by recrystallization from alcohol, may be employed if desired.

Alternatively, the Michael addition product may be dissolved in an aqueous solution for the cyclization reaction. Normally, the cyclic peptide product, being less soluble than the addition product, is readily precipitated from the reaction medium as it forms and is recovered by filtration or other suitable means.

Heating of the addition product is generally detrimental to the formation of cyclic peptides and results instead in linear oligomer formation.

SPECIFIC EMBODIMENTS

Having described the invention the following examples are provided as further illustrative and are not to be construed as limiting.

EXAMPLE 1

1,4,8,11-Tetraazacyclotetradecane-5,12-dione

Methyl acrylate (344 g, 4.0 moles) was added dropwise into neat ethylenediamine (240 g, 4.0 moles) while stirring. Addition was conducted at such a rate that the reaction temperature did not exceed 45° C. Addition time was 4.0 hours. The crude colorless product, N-(2-aminoethyl)-$\beta$-alanine methyl ester (580 g), was dissolved in deionized water to give a concentration of about 25 weight percent. Allowing the solution to stand at room temperature for 2–3 days caused a white solid product to slowly precipitate. The product was obtained as a fine white powder, m.p. 198° C.–199° C. Spectral analysis confirmed the product's structure as

EXAMPLE 2

The reaction condtions of Example 1 were substantially repeated excepting that the ester reactant was ethyl acrylate. Accordingly, ethyl acrylate (100 g, 1.0 mole) was added dropwise into neat ethylenediamine (60 g, 1.0 mole) while stirring. The reaction temperature was not allowed to exceed 55° C. and was completed over a period of 1.25 hours. The colorless, slightly sweet smelling liquid product weighed 160 g (100 percent yield). Distillation of this product gave a major fraction boiling at 180° C.–143° C./2 mm, weight 42.4 g which was identified as N-(2-aminoethyl)-$\beta$-alanine ethyl ester. Allowing this fraction to stand at room temperature caused it to transform to a white, slushy, semi-solid which weighed 4.05 g (9.56 percent) after filtration. Recrystallization from hot ethanol gave 1.25 g of fine fluffy white powder, m.p. 192° C.–193° C. which was spectroscopically identical to the product obtained in Example 1.

EXAMPLE 3

6,13-Dimethyl-1,4,8,11-tetraazacyclotetradecane-5,12-dione

Ethylenediamine (240 g, 4.0 moles) was placed in a 1000-ml 3-neck round-bottom flask equipped with air stirrer, addition funnel and reflux condenser. Methyl methacrylate (400 g, 4.0 moles) was added at room temperature over a 1-hour period. The product, a mixture of N-(2-aminoethyl)-$\alpha$-methyl-$\beta$-alanine methyl ester and methanol, was allowed to sit at room temperature for 2 weeks during which time a white crystalline precipitate formed.

The precipitate was isolated by filtration and recrystallized from ethanol. The compound melted with decomposition at 260° C.–261° C. Elemental analysis yielded C-56.1 percent, H-9.32 percent, and N-21.8 percent. This compares well with the theoretical ratio of 56.22:9.44:21.86 for the macrocyclic dimer. The mass as determined by chemical ionization mass spectroscopy was 256 as further confirmation of the structure.

What is claimed is:

1. A process for preparing a cyclic peptide corresponding to the formula

comprising contacting an acrylic ester of the formula $CH_2=CR'CO_2R''$ with a 1,2-alkylenediamine of the formula $NH_2CRHCRHNH_2$ wherein R and R' are independently each occurrence hydrogen or $C_{1-4}$ alkyl, and R'' is $C_{1-8}$ alkyl under reaction conditions conductive to the formation of a Michael addition product and thereafter subjecting the Michael addition product to a temperature between about 10° C. and about 60° C. for a time sufficient to form the cyclic peptide.

2. The process of claim 1 wherein the acrylic ester is contacted with the 1,2-alkylenediamine at a temperature from about −10° C. to about 80° C. in the absence of a solvent.

3. The process of claim 2 wherein the temperature is from about 20° C. to about 60° C.

4. The process of claim 1 wherein the Michael addition product is subjected to a temperature of from about 10° C. to about 60° C. for a time up to about several weeks.

5. The process of claim 1 wherein the acrylic ester is methyl acrylate, ethyl acrylate, methyl methacrylate or ethyl methacrylate and the 1,2-alkylenediamine is ethylenediamine.